United States Patent [19]

Knopf et al.

[11] Patent Number: 4,927,954
[45] Date of Patent: May 22, 1990

[54] CONTINUOUS PROCESS FOR PRODUCING SECONDARY ALCOHOLS AND CARBOXYLIC ACID ESTERS

[75] Inventors: Robert J. Knopf, St. Albans; Louis F. Theiling Jr., Charleston, both of W. Va.; Leroy P. Berti, Houston, Tex.

[73] Assignee: Union Carbide Chemicals and Plastics Company, Inc., Danbury, Conn.

[21] Appl. No.: 341,270

[22] Filed: Apr. 19, 1989

Related U.S. Application Data

[63] Continuation of Ser. No. 198,245, May 25, 1988, abandoned, which is a continuation of Ser. No. 508,561, Jun. 28, 1983, abandoned.

[51] Int. Cl.$^5$ .................. C07C 67/04; C07C 67/02; C07C 27/00
[52] U.S. Cl. .................. 558/441; 558/443; 560/152; 560/179; 560/187; 560/205; 560/226; 560/227; 560/234; 560/247; 568/840; 568/876
[58] Field of Search ............ 560/152, 179, 187, 205, 560/226, 227, 234, 247; 558/441, 443; 568/840, 876

[56] References Cited

U.S. PATENT DOCUMENTS

| | | | |
|---|---|---|---|
| 2,414,999 | 1/1947 | Bearse et al. | 260/410.9 R |
| 2,415,000 | 1/1947 | Bearse et al. | 560/70 |
| 3,037,052 | 5/1962 | Bortnick | 260/485 |
| 3,098,093 | 7/1963 | Hagemeyer et al. | 560/234 |
| 3,299,110 | 1/1967 | Pine | 560/247 |
| 3,579,309 | 5/1971 | Sennewald et al. | 560/234 |
| 3,644,497 | 2/1972 | Mesich | 560/226 |
| 3,700,726 | 10/1972 | Johnson et al. | 260/491 |
| 4,260,813 | 4/1981 | Kametaka et al. | 560/234 |
| 4,293,499 | 10/1981 | Hughes | 560/247 |
| 4,370,491 | 1/1983 | Bott et al. | 203/DIG. 6 |
| 4,384,148 | 5/1983 | Schmidt | 568/907 |
| 4,431,838 | 2/1984 | Feldman et al. | 203/DIG. 6 |

FOREIGN PATENT DOCUMENTS

| | | |
|---|---|---|
| 2031421 | 4/1980 | United Kingdom . |
| 2041364 | 9/1980 | United Kingdom . |
| 8100846 | 4/1981 | United Kingdom . |

OTHER PUBLICATIONS

Rohm and Haas, "Amberlyst 15" Technical Bulletin No. IE-94-65/72/76, Sep. 1978, pp. 1-17.

*Primary Examiner*—Warren B. Lone
*Assistant Examiner*—Vera C. Clarke
*Attorney, Agent, or Firm*—Gerald L. Coon

[57] ABSTRACT

A continuous process for efficiently co-producing secondary alcohols of long-chain olefins and lower carboxylic acid esters, comprising (I) performing an acid/olefin reaction in the presence of a heterogeneous catalyst such as Amberlyst 15, and (II) performing an ester-exchange reaction in the presence of, e.g., titanium alcoholate. A desirable feature of the process is the ability to produce co-products of choice.

15 Claims, No Drawings

CONTINUOUS PROCESS FOR PRODUCING SECONDARY ALCOHOLS AND CARBOXYLIC ACID ESTERS

This application is a Continuation of prior U.S. application Ser. No. 198,245 Filing Date May 25, 1988 now abandoned and/which is a continuation of application Ser. No. 508,561 Filing Date Jun. 28, 1983 now abandoned.

BACKGROUND OF THE INVENTION

1. Technical Field

This invention relates to the continuous production of linear, secondary aliphatic alcohols, with co-production of carboxylic acid esters, from selected olefins, alcohols and carboxylic acids. This is achieved by two reactions in sequence: (1) the reaction between α-olefins and carboxylic acids, and (2) a transesterification reaction.

2. Description of the Prior Art

The oxylation of olefins by carboxylic acids has long been known in general terms: however, catalysis has been problematical and full commercial success has been elusive. More specifically, homogeneous, strong acid catalysis of the olefin/carboxylic acid reaction is well known (see U.S. Pat. Nos. 2,414,999 and 2,415,000), but suffers from problems of poor efficiency and troublesome product isolation attributable to extensive by-product formation through olefin dimerization and oligomerization reactions (cf. Rohm & Haas Co. Technical Bulletin entitled "Amberlyst® 15, "Fluid Process Chemicals Group, Sept. 1978). Furthermore, since the equilibrium constant for the olefin/carboxylic acid addition reaction decreases rapidly with increasing chain length of the olefin (cf. U.S. Pat. No. 3,037,052), this reaction has generally been considered impractical for olefins in the detergent range of $C_{11}$–$C_{16}$. Attempts have been made to overcome the problems inherent with homogeneous catalysis by using heterogeneous catalysts of the strong acid type, such as sulfonated styrene/divinyl benzene copolymers. However, the gel-type ion-exchange resins were ineffective catalysts for the reaction, whereas the macroreticular type resins were effective catalysts for the reaction with α-olefins, but not for the reaction with the internal olefin species which are formed during the reaction by isomerization.

One object of the present invention, therefore, is to provide for the efficient catalysis of the reaction between certain α-olefins, and their internal isomers, and certain carboxylic acids.

Transesterification and reactive distillation are each individually known in a variety of processes. Transesterification is virtually always practiced as a batch reaction with rather large quantities of one reactant being used to drive the reaction toward completion by mass action displacement of the equilibrium.

Another commonly used approach is that of equilibrium displacement by removal of product or coproduct as it is formed in the system; frequently this can be accomplished via an azeotropic distillation. Continuous transesterification has been practiced, but in only few instances and then only under circumstances decidedly favorable to the reaction. For example, one system has been described for continuously ester-exchanging 1,4-butanediol diacetate with methanol to coproduce 1,4,-butanediol and methyl acetate (cf. German patent application No. 2,820,521 to BASF-AG or British patent application No. 2,031,421 to Japan Synthetic Rubber). A second system (cf. U.S. Pat. No. 4,260,813 to Showo Denko K.K.) has been described for continuously producing ethylene glycol monoethyl ether acetate from ethylene glycol monoethyl ether and ethyl acetate. In both of these systems, conditions for exchange are favorable because the esters being exchanged are derived from reactive primary hydroxyl groups. A particularly significant attribute of the prior art systems, however, is that they need not react to substantial completion because the higher molecular weight alcohol and ester couples used as reactants can be separated by conventional distillation. Such separation is not possible in the systems of the present invention because the acetate esters of typical detergent range alcohols, such as the tridecyl and tetradecyl alcohols, boil at the same temperature as the corresponding alcohols, and the downstream conversion of the product secondary alcohols, into high-performance surfactant-range alcohols requires substantially pure alcohol reactants.

Thus, another object of the present invention is to provide for the efficient transesterification of the reaction products of olefins and carboxylic acids to produce desired alcohols and by-product carboxylic acid esters.

Both reactions employed in this process are chemically reversible; i.e., under usual conditions they reach equilibrium at a point short of complete conversion. Generally speaking, such reactions are not well-suited to multi-step, continuous process operation; that two such reactions are employed in the continuous process of this invention is, therefore, unique in itself. Moreover, both reactions exhibit certain other characteristics which under the usual circumstances would render them unattractive candidates around which to develop a continuous process. For example, the carboxylic acid/α-olefin reaction of step (1), above, is generally considered to present problems of (1) decreasing equilibrium constant with increasing size of olefin, (2) by-product formation (efficiency loss) through olefin oligomerization/polymerization, and (3) poor structural selectivity in the product (multiplicity of positional isomers, all secondary are formed) because of olefin isomerizations which accompany the desired acid/olefin addition reaction. Accordingly, this reaction would not generally be considered an attractive choice for inclusion in a continuous process route to long-chain alcohols. Similarly, the transesterification reaction of step (2), above, is generally considered to be useful only in cases where (1) incomplete conversions are acceptable, (2) large excesses of one reactant may be used to drive the reaction in the desired direction, or (3) the equilibrium position can be displaced by continual removal of either product or coproduct. Thus transesterification, although generally a clean, efficient reaction, is typically practiced only as a batch operation.

Accordingly, an additional object of the present invention is the development of an economically superior, highly efficient, environmentally clean, continuous process utilizing the reaction sequence described above.

SUMMARY OF THE INVENTION

It has now been found that these and other worthwhile objects can be met by a continuous process for co-producing higher secondary alcohols and lower carboxylic acid esters from long-chain olefins and lower carboxylic acids, comprising the steps of:

(A) passing a long-chain α-olefin or mixture, (optionally in a mixture with the internal olefin isomers thereof) together with a lower carboxylic acid through a reaction zone in the presence of an acidic heterogeneous catalyst under conditions at which the corresponding oxylation reaction will occur and thereby producing secondary alcohol carboxylates and isomers thereof;

(B) recovering the carboxylates and isomers thereof produced in step (A);

(B') optionally, the additional step of mixing the recovered carboxylates and isomers thereof with a lower aliphatic alcohol in a pre-reaction zone in the presence of an ester exchange catalyst under conditions at which pre-reaction will occur;

(C) passing the recovered carboxylates and isomers thereof together with a lower aliphatic alcohol through a reactive distillation still in the presence of an ester-exchange catalyst under conditions at which the ester exchange will occur and thereby producing, as coproducts, secondary alcohols of said long-chain olefins and carboxylates of said lower aliphatic alcohol; and (D) removing said secondary alcohols predominantly in the tails stream and said carboxylates predominantly in the overhead stream.

The process of this invention is uniquely suited to the production of linear, secondary alcohols of the type which are used commercially as hydrophobes in the preparation of high-performance, speciality, nonionic surfactants. Alcohols of this type are expensive to manufacture; at the present time they are available only through controlled paraffin oxidation processes which exhibit rather poor selectivity and chemical efficiency.

The present process represents a decidedly superior route to detergent-range, secondary alcohols. The products obtained from this process have all the structural characteristics desirable for speciality surfactant hydrophobe service, namely, a distribution of carbon numbers within the general range of $C_{12}$–$C_{15}$ linear chains with all secondary hydroxyl functionality, and a broad isomer distribution. In addition, these products are free of troublesome (e.g., color-forming) impurities, such as carbonyl compounds which are generally present in alcohols derived from oxidation processes. The properties and performance characteristics of surfactants derived from hydrophobes made via this process match or surpass those of counterparts made from paraffin oxidation-derived hydrophobes.

The overall utility of the present process is enormously enhanced by the simultaneous production, in the ester exchange step, of commercially valuable coproducts in a high state of purity. Inasmuch as there is considerable latitude available in terms of coproduct selection, the manufacturer can operate his facility in whatever coproduct mode best fits his coproduct business needs at a given point in time. Thus, the process is truly unique in terms of flexibility, efficiency, and environmental cleanliness. In turn, these factors all contribute to the economic superiority exhibited by this process over alternate routes to detergent-range, secondary alcohols.

DETAILED DESCRIPTION OF THE INVENTION

This invention concerns a novel process for coproducing two commercially valuable classes of organic compounds, namely, (1) linear, secondary, aliphatic alcohols in the $C_{10}$–$C_{16}$ carbon number range, and (2) lower ($C_1$–$C_6$) carboxylic acid esters of lower ($C_1$–$C_8$), linear, branched, or cyclic aliphatic alcohols. The $C_{10}$–$C_{16}$ 2° alcohols provided by this process are widely used as intermediates ("hydrophobes") in the manufacture of speciality, high-performance, non-ionic and anionic surface active agents. The coproduct carboxylic acid esters of the lower aliphatic alcohols are used commercially as solvents, monomers, chemical intermediates, fragrances, etc. The process of the present invention is unique in that not only does it afford valuable products and coproducts, but also in that it is environmentally cleaner than, and economically superior to, existing processes. Additionally, this process is highly flexible in terms of the coproduct moiety while simultaneously being structurally selective in terms of the product moiety.

The following equations illustrate the sequence of reactions comprising the process and the types of products and coproducts which result from its practice:

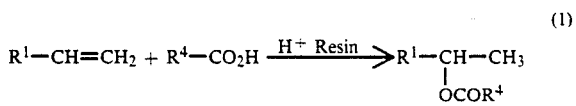

(1)

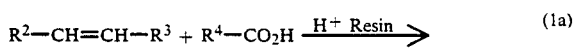

(1a)

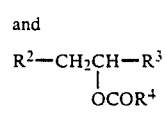

and

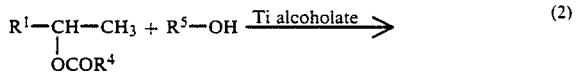

(2)

wherein $R^1$ is a $C_8$–$C_{14}$ radical, preferably a $C_{10}$–$C_{12}$ radical; $R^2$ and $R^3$ are linear, unsubstituted radicals whose chain lengths satisfy the relationship $R^2 + R^3 = C_8$–$C_{14}$; $R^4$ is a $C_1$–$C_5$ radical, preferably a $C_1$–$C_2$ radical; and $R^5$ is a $C_1$–$C_8$ radical, preferably a $C_2$–$C_4$ radical, either linear, branched, or cyclic. Thus, if $R^1 = \alpha\text{-}C_{12}H_{25}$, $R^4 = CH_3$ and $R^5 = n\text{-}C_4H_9$, the example shows the formation of sec.-tetradecanol (mixture of several isomers) as the product and n-butyl acetate as the coproduct. The titanium alcoholate can be any of those catalytically active species known to the art; however, it is preferred that the alcoholate be that corresponding to the reactant alcohol, i.e., $R^5\text{-OH}$.

Through the wide latitude possible in choice of $R^4$ and $R^5$, the process exhibits exceptional flexibility in terms of the coproduct ester. At the same time, the process exhibits structural selectivity in terms of the product alcohol because it leads exclusively to secondary isomers of linear structure.

In the continuous process of this invention, olefin and carboxylic acid are brought together in a reaction zone at the head end of the process train while 2° alcohol and coproduct ester are simultaneously recovered from appropriate distillation columns at the tail end of the process train. A particularly advantageous feature of the process of this invention is its simplicity. For example, the only operations (other than the reactions themselves) which are required between the head and tail ends of the process train are several continuous distillations which serve to remove/separate unreacted raw materials for recycle.

The process of this invention is generally described as follows, using for purposes of illustration the case wherein a mixture of $C_{13}/C_{14}$ α-olefins, acetic acid and n-butanol are the raw materials, a mixture of secondary $C_{13}/C_{14}$ alcohols (mixed isomers) is the product, and n-butyl acetate is the coproduct.

It is optional, but desirable, to insert prior to the oxylation step a pre-reaction "clean-up" reactor to remove tramp metal ions. This may desirably be a bed packed with the oxyalkylation catalyst, e.g., Amberlyst 15, but operated at a relatively low temperature, e.g., ~60° C. This temperature is chosen to be below the reaction temperature of the oxyalkylation reaction; thus, the catalyst acts essentially as an ion exchange resin instead of an oxylation catalyst.

A preheated mixture of acetic acid (in excess, preferably) and $C_{13}/C_{14}$ α-olefins is passed first through an ion-exchange resin bed and then through one or more heated, fixed-bed type reaction zones containing strongly acidic resin(s) as catalyst(s). Temperature and pressure in the oxylation step are not considered narrowly critical, but should be chosen to maintain all reactants in the liquid phase. Conversion rate will increase with increasing temperature, but catalyst deterioration will also thereby be accelerated. The homogeneous effluent from the reaction zone(s) contains unreacted acetic acid, unreacted $C_{13}/C_{14}$ olefins (in partially isomerized form), and multiple isomers (all secondary) of the acetates of tridecyl and tetradecyl alcohols. A typical range for olefin conversion is 20-35%; the actual conversion achieved is dependent upon a host of variables including temperature, residence time in the reactor, acid: olefin mol ratio, catalyst, catalyst age, extent of isomerization in the recycle olefin feed, etc., but must necessarily be <100% because of the reversible nature of the reaction.

The homogeneous effluent from the reactor(s) is pumped directly into the column section of a stripping still (operated at or below atmospheric pressure) wherein acetic acid is flashed overhead and recycled to the reaction system while a substantially acid-free effluent is removed from the base of the still. This stream is pumped into the mid- or upper-column section of a vacuum stripping still wherein partially isomerized $C_{13}/C_{14}$ olefins are recovered overhead for recycle to the reaction system while a substantially olefin-free effluent is removed from the base of the still. When this stripping still is operating in a steady-state mode at the appropriate conditions of temperature, pressure, feed rate and reflux ration, both the overhead and the bottoms stream will contain <2% contaminants.

The effluent from the base of the olefins/acetates separation still is mixed in-line with pre-dried n-butanol and a typical ester exchange catalyst, such as tetrabutyl titanate, in the desired proportions and the resulting mix is allowed to undergo pre-reaction in a vessel of the continuous stirred tank reactor (CSTR) type. The effluent from this pre-reactor is then pumped to the upper column section of a reactive distillation still while additional n-butanol is vaporized into the base of the still column. Transesterification occurs in the column, each tray acting as a reaction stage. The still is operated on a total make basis (i.e., no reflux), butanol and coproduct butyl acetate being removed overhead continuously (these two species form an azeotrope) while an effluent stream consisting predominantly of $C_{13}/C_{14}$ secondary alcohols and $C_{13}/C_{14}$ titanate is removed continuously from the reboiler at the base of the still. Other components (minor) of the still base stream include butanol, butyl acetate and unreacted tridecyl/tetradecyl acetate. When this still is operating in a steady-state mode at the desired conditions of temperature, reactants mol ratio, and residence time, conversion of acetates to alcohols is typically at least about 97.5% and butyl acetate concentration in the still base effluent is less than about 0.5%. Generally speaking, the butanol concentration in the still bottoms stream will average about 5-10%. Operating temperature in the transesterification column is not considered critical. Elevated temperatures can be used to obtain more rapid reaction rates, but temperatures will be limited primarily by the pressure limitations of the equipment. It should be appreciated, however, that elevated pressure may affect the composition of any azeotrope formed. For example, in the case of the butanol/butyl acetate azeotrope, higher column pressures result in an azeotrope richer in butanol. While the selection of a transesterification catalyst is not considered critical, compounds of titanium are preferred since they are neutral, non-corrosive liquids which leave no inorganic residue. The titanates may be either simple, mixed or partially hydrolyzed. Also useful are, e.g., the alkoxides of sodium and zirconium.

The still bottoms stream from the reactive distillation column is fed into a stripping still (atmospheric or subatmospheric) where butanol and butyl acetate are recovered overhead and combined with the overhead material from the reactive distillation still. The combined stream can either be used directly as partially converted feedstock in the manufacture of butyl acetate by esterification or separated into its components by known processing techniques for ultimate sale of the butyl acetate and for recycle of the butanol back to the transesterification column.

The still bottoms stream from the butanol/butyl acetate stripping still is fed to an appropriate vacuum stripping system (e.g., a conventional evaporator, a thin-film or wiped-film evaporator, or some combination of these) for recovery of secondary tridecyl/tetradecyl alcohols (in the form of mixed isomers) overhead and for recycle of titanium alcoholate catalyst residues back to the transesterification pre-reactor. The $C_{13}/C_{14}$ secondary alcohol mixture is used directly as a hydrophobe in the manufacture of non-ionic surfactants (or as an intermediate in the manufacture of anionic surfactants); these conversions are accomplished by known art procedures however, and this technology does not constitute a part of the present invention.

In view of the foregoing discussion regarding catalysts, it was unexpected that certain heterogeneous, strong acid resins are very effective catalysts for the carboxylic acid/higher olefins reaction. These resins not only catalyze the acid reaction with both the α-olefins and the internal olefins, but they do so at rates which permit their use in a packed (fixed) bed mode where contact times must necessarily be rather short. Thus, these resins are ideally suited for continuous process service. As heterogeneous catalysts, these resins offer all the other advantages inherent in such materials, e.g., ease of handling and storage, elimination of catalyst removal problems, regeneratability, low unit cost, low corrosivity, and ease of ultimate disposal through land-fill measures, among others. In the present process, the formation exclusively of secondary esters (as a mixture of isomers) from either α-olefins or internal olefins is desirable because the properties of the surfactants derived from the secondary alcohol products are enhanced by the presence of a multiplicity of isomers.

Two classes of strong acid resins can be used as catalysts in the acetoxylation step of the instant process, namely, (1) copolymeric, high flourine content aliphatic sulfonic acids of the type exemplified by DuPont's Nafion ® H, and (2) macroreticular, cross-linked sulfonated styrene/divinyl benzene copolymers of the type exemplified by Rohm and Haas' Amberlyst ® 15, Amberlyst XN-1005, Amberlyst XE-372, etc. The macroreticular resins are particularly preferred catalysts because they are readily available, relatively inexpensive, and easily amenable to structural modification in order to "tailor" the catalyst for optimum performance in a specific reaction system. It should be emphasized that not all macroreticular, strong acid resins will function as effective catalysts in the process of this invention. Physical properties such as resin porosity, surface area and crosslink density are enormously important in determining the suitability of a given resin for use with a given reaction system. Catalyst selection will be a matter of choice, and selection of specific physical properties will depend upon the particular reactants involved. It may be said in general that the physical properties of the catalyst must be such as to permit ready diffusion of the reactant molecules into the catalyst structure to permit adequate contact with the catalytically active surfaces. Cross-link density is considered to be particularly significant in this regard since it directly affects how much the catalyst resin can swell. In the case of styrene/divinyl benzene copolymers, cross-link density is considered to be directly related to the amount of divinyl benzene present. In general, a cross-link density in the range of about 18–21% will produce good results, while a cross-link density of about 12% or less will be unsatisfactory. Similarly, a pore volume of more than about 30%, preferably about 30–35%, is desirable.

Olefins suitable for use as raw materials in this process for manufacturing detergent-range secondary alcohols are the linear, terminal species of type (I) below and the linear, internal species of type (II) below.

(I) $R^1\text{-CH}=CH_2$ (II) $R^2\text{-CH}=CH\text{-}R^3$

The type (I) olefins (so-called α-olefins) are the primary species used initially in the process; however, the type (I) olefins are partially isomerized into the type (II) olefins by the acidic resin bed in the reaction zone; consequently, the type (I) and type (II) olefins are both present in the recycle process stream. It is this concurrent isomerization reaction which is responsible for the broad isomer distribution present in the product secondary alcohols. For olefins of type (I), $R^1$ = a linear, unsubstituted alkyl radical of from 8–14 carbon atoms (i.e., n-octyl through n-tetradecyl); in the type (II) olefins, $R^2$ and $R^3$ are linear, unsubstituted alkyl radicals whose chain lengths must satisfy the relationship $R^2+R^3=C_8\text{-}C_{14}$. The number of internal isomers possible in olefins of type (II) is 4 with decene and undecene, 5 with dodecene and tridecene, 6 with tetradecene and pentadecene, and 7 with hexadecene. In the practice of the invention, mixtures of olefins are desirably employed because this approach gives the best performance characteristics in the surfactant product. For example, mixtures of 12, 13, and 14 carbon species are often ideal in surfactant applications. Due to certain separations which must be performed in this process, mixtures containing more than 2 adjacent carbon number species are best prepared by blending the products from separate runs, each made with mixtures of species two or less carbon numbers wide. Thus, if a $C_{12}$-$C_{15}$ secondary alcohol is desired, the preferred approach is to combine (blend) the products from separate runs made with a $C_{12}/C_{13}$ olefins mixture and a $C_{14}/C_{15}$ olefins mixture. The stipulation that $R^1$, $R^2$ and $R^3$ in the generic formulae (I) and (II) be linear is made from a final product (surfactant) performance viewpoint only; branched hydrophobe structures are generally less desirable than their linear counterparts because they are more difficulty biodegradable and therefore less "clean" environmentally. In practice, minor amounts of branched structures will be present in the final product because the "linear α-olefin" feedstocks derived from petroleum cracking often contain small quantities of branched materials which arise from skeletal rearrangements which occur during the cracking operations. Thus, the stipulation that the olefin feedstocks be linear is not made with the intention of excluding from process suitability linear olefins having minor content of branched structures. Rather, the intention is to emphasize the desirability of avoiding intentional introduction of branched structures into the olefin feedstocks.

Carboxylic acids suitable for use in the process of this invention are those of generic structure $R^4\text{-}CO_2H$ wherein $R^4$ may be hydrogen, an alkyl or an alkenyl radical, linear or branched, saturated or unsaturated, containing from 1–5 carbon atoms, e.g., methyl, ethyl, propyl, isopropyl, n-butyl, isobutyl, vinyl, etc. Further, the radical $R^4$, when not hydrogen, can be substituted by one or more other functional groups which are inert under the conditions of the process. Such functional groups include chlorine, bromine, alkoxy, thioalkoxy, cyano, carboxyamido, and the like. When $R^4$ is an alkenyl radical, the double bond should lie α, β-to the —$CO_2H$ group. Examples of specific carboxylic acids which are suitable for use in the process include cyanoacetic acid, the mono-, di-, and trichloroacetic acids, methoxyacetic acid, triflouroacetic acid, 3-methylmercaptopropionic acid, acrylic acid, methacrylic acid, 2-cyanoacrylic acid, 2-chloroacrylic acid, and β-acryloxypropionic acid, to mention only a few.

Alcohols which are suitable for use in the process of this invention are those of generic structure $R^5\text{-}OH$ wherein $R^5$ may be a linear or branched alkyl or alkenyl radical of from 1 to 8 carbon atoms, optionally substituted with other functional groups which are inert under the conditions of the process. Thus, other functional groups which can be present as substituents on the $R^5$ alkyl or alkenyl radical are the same ones which are suitable for use as substituents on the $R^4$ radical of the carboxylic acid reactant. Specific examples of alcohols which may be used in this process are methanol, ethanol, isopropanol, n-propanol, isobutanol, n-butanol, allyl alcohol, 3-butene-2-ol, 2-cyanoethanol, 2-chloroethanol, 2-ethoxyethanol, 3-chloropropanol, 2-fluoroethanol, methallyl alcohol, 2-butanol, and 2-ethylhexanol, to name but a few. In the alcohol moiety, unsaturation, if present, need not be located in any specific position relative to the —OH group.

Theoretically, the number of acid/alcohol combinations which are possible with this invention is very large. Practically, however, the number is fairly small because only relatively few of the coproducts possible are valuable articles of commerce enjoying large, established markets. In this regard, the esters of acetic, acrylic, and methacrylic acids are particularly valuable coproducts for which large markets exist as solvents and monomers, respectively. Thus, coproducts such as ethyl, n-propyl, isopropyl, n-butyl, isobutyl, allyl, amyl and 2-ethoxyethyl acetates are particularly preferred species along with ethyl acrylate and the butyl acrylates, 2-ethylhexyl acrylate and methyl methacrylate. When all factors are taken into consideration, the most preferred coproducts in this process are the low alkyl esters of acetic acid.

EXAMPLES

The following examples are intended to illustrate the invention, but not in any way limit it.

EXAMPLE 1

This example illustrates the preparation of a mixture of secondary dodecyl acetates and secondary tetradecyl acetates by passing a 2:1 molar mixture of glacial acetic acid and Ethyl Corp. $C_{12}/C_{14}$ α-olefins (67/33% by weight) through a fixed bed reactor containing a polymeric, strongly acidic resin as catalyst. In Part A, the catalyst was Rohm & Haas' Amberlyst 15, a macroreticular, sulfonated styrene/divinylbenzene copolymer supplied in the form of beads having particle sizes in the range of 300–1000 microns. In Part B, the catalyst was DuPont's Nafion H, a perflourinated, aliphatic, sulfonic acid copolymer supplied in the form of granules having particle sizes from 300–500 microns. These catalysts were placed in a ¼"×60" stainless steel coil (volume ~25 cc) containing plugs of glass wool at both ends: the Amberlyst 15 charge was 14 grams while the Nafion H charge was 22 grams. The coil reactor was connected to a coil preheater; both reactor and preheater coils were contained within a pipe through which was circulated a heat exchange fluid maintained at the desired reactor temperature. The acetic acid/α-olefins mixed feedstock, pre-heated to 70° C. to ensure homogeniety, was pumped through the preheater and then the reactor coil at 40 psig pressure and various desired rates using a piston type pump with Teflon ® seals. The crude reaction effluent was optionally collected in a receiver and analyzed directly or passed into a vacuum stripping vessel for removal of acetic acid prior to analysis. In the particular experiments covered by this example, the former analytical approach was used. Analyses were performed instrumentally using a gas chromatograph equipped with a Carbowax ® 20M/Chromosorb ® T column.

The above-described reaction system was operated for 5 days (8-hour days) on each of the catalysts. Table I contains a summary of results obtained during the third day of operation with each of these catalysts. In addition to demonstrating the feasibility of carrying out the higher olefin/carboxylic acid addition reaction with certain strongly acidic fixed bed catalysts, the results show the effects of residence (contact) time on both conversion and on product isomer distribution. It will be noted both that multiple isomers are formed in the reaction and that all isomers formed are of secondary structure. Both of these factors are important in terms of the anticipated end use (surfactants) of the secondary alcohol products of this process. The isomer distribution values cited in the tabulated data were normalized to a value of 1.0 for the major isomer formed, the 2-isomer (i.e., 2-dodecyl acetate and 2-tetradecyl acetate). By NMR analysis, the second most prevalent isomer is the 3-isomer and the least prevalent isomer is the 4-isomer.

TABLE I

SECONDARY ALCOHOL HYDROPHOBES
COMPARISON OF AMBERLYST 15 WITH NAFION H AS
FIXED BED CATALYSTS FOR $C_{12}/C_{14}$ OLEFIN ACETOXYLATION[a]

| Catalyst | Amberlyst 15 | | | | | Nafion H | | | | |
|---|---|---|---|---|---|---|---|---|---|---|
| | 3 | 4 | 2 | 6 | 5 | 1 | 5 | 2 | 3 | 4 |
| Feed Rate, cc/min. | 1.81 | 2.42 | 2.46 | 3.49 | 4.70 | 1.22 | 1.72 | 2.77 | 3.84 | 5.35 |
| Contact Time, min. | 13.8 | 10.3 | 10.1 | 7.2 | 5.3 | 20.5 | 14.5 | 9.0 | 6.5 | 4.7 |
| Esters Content in Product, Area % | 25.31 | 23.72 | 22.91 | 19.04 | 16.07 | 26.36 | 25.52 | 24.93 | 22.81 | 19.0 |
| Conversion, % of Theory, Olefin Basis | 31.64 | 29.65 | 28.64 | 23.80 | 20.88 | 37.95 | 31.9 | 31.16 | 28.51 | 23.79 |
| Molar Ratio, $C_{12}$:$C_{14}$ Olefin | | | | | | | | | | |
| Charged | ← | ← | 2.01 | → | → | ← | ← | 2.01 | → | → |
| Reacted | 2.57 | 2.69 | 2.77 | 3.02 | 3.13 | 2.16 | 2.56 | 2.59 | 2.79 | 2.99 |
| Weight Ratio, $C_{12}$:$C_{14}$ Olefin | | | | | | | | | | |
| Charged | ← | ← | 1.72 | → | → | ← | ← | 1.72 | → | → |
| Reacted | 2.23 | 2.41 | 2.48 | 2.68 | 2.77 | 1.91 | 2.27 | 2.32 | 2.49 | 2.65 |
| Isomer Distribution, G.C.[c] | | | | | | | | | | |
| $C_{12}$ Esters | | | | | | | | | | |
| 4-isomer | 0.28 | 0.24 | 0.22 | 0.18 | 0.17 | 0.84 | 0.33 | 0.36 | 0.24 | 0.20 |
| 3-isomer | 0.39 | 0.36 | 0.35 | 0.31 | 0.29 | 0.51 | 0.38 | 0.39 | 0.33 | 0.29 |
| Isomer 3 | 1.0 | 1.0 | 1.0 | 1.0 | 1.0 | 1.0 | 1.0 | 1.0 | 1.0 | 1.0 |
| $C_{14}$ Esters | | | | | | | | | | |
| 4-isomer | 0.14 | 0.11 | 0.11 | 0.08 | 0.07 | 0.56 | 0.21 | 0.22 | 0.16 | 0.12 |
| 3-isomer | 0.31 | 0.29 | 0.28 | 0.25 | 0.23 | 0.45 | 0.32 | 0.33 | 0.28 | 0.26 |
| Isomer 3 | 1.0 | 1.0 | 1.0 | 1.0 | 1.0 | 1.0 | 1.0 | 1.0 | 1.0 | 1.0 |

[a] Operating Conditions: Temperature, 132° C.; Acid:Olefin Ratio, 2:1; Reactor Volume, 25 cc; 3rd Day of Operation; Catalyst Weights in Reactor, 22 Grams Nafion, 14 Grams Amberlyst.
[b] Area % Values from G.C. Normalized to Major Isomer = 1.0; Major Isomer According to NMR is the 2-Isomer.
[c] G.C. Column: 2 Meters × ⅛" ss packed with 7% CARBOWAX 20M on 40/60 Chromosorb T.

EXAMPLE 2

This example illustrates the preparation of a mixture of secondary tridecyl and tetradecyl alcohol acetates by passing a 2:1 molar mixture of glacial acetic acid and Chevron Corp. $C_{13}/C_{14}$ α-olefins (48/52 w/w %) through a laboratory size, shell-and-tube bundle heat exchange vessel used as a fixed bed reactor. The heat exchanger consisted of 60×¼"×12" Type 316 SS.

tubes, of which 30 were packed with Amberlyst 15 resin to a total catalyst charge of 60 grams. In order to permit resin expansion to occur, the tubes were packed to only about 50% of their free volume. Temperature in the reactor was controlled by circulating a heat exchange fluid of desired temperature through the shell side of the reactor; pressure was maintained at 40 psig, as in Exam- Example 2 demonstrates (1) the use of another olefin mixture ($C_{13}/C_{14}$ mix derived from petroleum wax-cracking versus $C_{12}/C_{14}$ mix of the Example I derived from ethylene growth reaction), (2) the suitability of another design of fixed bed reactor, (3) the use of a pre-reaction sieve bed to clean up the feedstock, and (4) the amenability of the catalyst to regeneration.

TABLE IIA

SECONDARY ALCOHOL HYDROPHOBES
ACETOXYLATION OF $C_{13}/C_{14}$ OLEFIN
IN MODIFIED FIXED BED REACTOR
INITIAL CYCLE OF AMBERLYST ® 15 CATALYST

| | Day No. | | | | | | | | | |
|---|---|---|---|---|---|---|---|---|---|---|
| | 1 | 2 | 3 | 4 | 5 | 6 | 7 | 8 | 9 | 10 |
| Residence Time, min[a] | 22.5 | 13.4 | 11.6 | 16.6 | 10.3 | 16.5 | 13.3 | 18.0 | 18.1 | 27.3 |
| Temperature, °C.[a] | 132.0 | 133.1 | 132.0 | 132.5 | 133.3 | 133.7 | 141.5 | 136.3 | 143.5 | 143.0 |
| Feed Rate, g/min | 2.16 | 3.59 | 4.13 | 2.89 | 4.67 | 2.90 | 3.60 | 2.66 | 2.65 | 1.76 |
| Total Effluent, g | 85 | 888 | 1128 | 675 | 1479 | 774 | 1426 | 897 | 1012 | 478 |
| Esters Content, Area % by GC | 24.02 | 27.49 | 27.45 | 26.96 | 23.25 | 23.17 | 21.99 | 19.46 | 18.0 | 22.50 |
| Conversion, % of Theory, Olefin Basis | 30.03 | 33.94 | 33.89 | 33.29 | 28.70 | 28.60 | 27.15 | 24.03 | 22.22 | 27.78 |
| Productivity (Cumulative), # Esters/# Catalyst[b] | 0.34 | 4.42 | 9.59 | 12.63 | 18.37 | 21.37 | 26.61 | 29.53 | 32.57 | 34.37 |

[a]Values given are averages which have been effluent-weighted to compensate for intentional changes in feed rates and temperatures during each day's operation.
[b]Based on 60 gram catalyst bed charge.

TABLE IIB

SECONDARY ALCOHOL HYDROPHOBES
ACETOXYLATION OF $C_{13}/C_{14}$ OLEFIN
IN MODIFIED FIXED BED REACTOR
REGENERATION CYCLE OF AMBERLYST ® 15 CATALYST

| | Day No. | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Residence Time, min[a] | 15.5 | 12.9 | 15.7 | 15.5 | 19.3 | 20.61 | 18.4 | 13.3 | 20.3 | 16.1 | 20.6 | 17.2 | 8.5 | 21.1 | 15.9 | 6.5 |
| Temperature, °C.[a] | 129.9 | 131.7 | 130.7 | 129 | 129 | 129.7 | 128.8 | 129 | 129 | 129 | 128.8 | 128.5 | 129 | 129 | 129 | 129.3 |
| Feed Rate, g/min | 3.13 | 3.67 | 3.11 | 3.21 | 2.53 | 2.38 | 2.71 | 3.77 | 2.49 | 3.09 | 2.39 | 3.04 | 5.73 | 2.34 | 3.11 | 5.87 |
| Total Effluent, g | 1865 | 1199 | 974 | 1420 | 1081 | 711 | 1140 | 1553 | 858 | 1398 | 1476 | 1468 | 783 | 667 | 1378 | 1337 |
| Esters Content, Area % by GC | 21.65 | 18.95 | 18.1 | 16.01 | 16.87 | 15.4 | 14.0 | 12.4 | 13.56 | 12.9 | 10.05 | 9.85 | 9.52 | 10.12 | 6.18 | 7.06 |
| Conversion, % of Theory, Olefin Basis | 26.73 | 23.4 | 22.35 | 19.76 | 20.83 | 19.0 | 17.28 | 15.31 | 16.74 | 15.93 | 12.41 | 12.16 | 11.75 | 12.49 | 7.63 | 8.71 |
| Productivity (Cumulative[b] from Initial Cycle-Table I), # Esters/# Catalyst | 41.11 | 44.91 | 47.85 | 51.65 | 54.7 | 56.53 | 59.2 | 62.42 | 64.36 | 67.37 | 69.85 | 72.27 | 73.52 | 74.65 | 76.07 | 77.65 |

[a]Values given are averages which have been effluent-weighted for each day of operation to correct for use of varying feed rates and temperatures.
[b]Cumulative productivities based upon both initial cycle of catalyst use and regenerated cycle of catalyst use.

ple 1. Prior to entering the reactor, the preheated acid-/olefin mixed feedstock was passed through a heated (70°–90° C.) column containing Linde ® AW-200 molecular sieves for purposes of removing any water present in the feedstock. Crude reaction product from the reactor was collected in a receiver and analyzed by gas chromatography, as described in Example I, except that the GC column in this case was packed with 10% Apiezon L on Chromosorb WAW/DMGS.

The above system was operated for 10 days (8-hour days) in the initial resin cycle, with the results shown in Table IIA. At this point the catalyst bed was regenerated by a procedure involving sequential steps of solvent wash (ethyl acetate), water wash, 10% aqueous sulfuric acid wash, water wash, and vacuum drying at 100° C./2 mm overnight. Following regeneration, the system was operated for an additional 16 days (8-hour days), with the results shown in Table IIB. For the total 26 days of operation, the productivity was 77.6 pounds of acetates per pound of catalyst. A total of 4 isomers each of the $C_{13}$ and $C_{14}$ olefins were formed in this reaction with the 2-isomers again being the most prevalent species.

EXAMPLE 3

Example 3A illustrates the preparation of the same products as Example 2 in the same reactor and with the same catalyst as used in Example 2. In Example 3A, however, the reactor temperature was only 118°–120° C., as compared with 129°–143° C. in Example 2, and the olefin feedstock was recovered (recycled) material from previous experiments, whereas the olefin feedstock used in Example 2 had been fresh (virgin) α-olefin. Thus, the Example 3 feedstock contained a large quantity (~50%) of internal double-bond species (arising from isomerization), whereas the Example 2 feedstock contained essentially only the more reactive terminal double-bond species. Thus, Example 3A reflects a fully continuous process, where unreacted olefins would be recycled back to the reactor continuously while makeup fresh olefin is added, the olefin feedstock, therefore, tending to reach a steady-state composition in terms of terminal/internal double-bond content.

The above-described system was operated for a total of 33 days (8-hour days), 26 of which were on the initial cycle of catalyst usage and 7 of which were on the regenerated cycle of catalyst usage. The total productivity for the 33 days of operation was 78.4 pounds of $C_{13}/C_{14}$ acetates per pound of catalyst; actual weight of products made was 10.58 pounds from 75.0 pounds of 2:1 molar ratio acid/olefin feed. The structural characteristics of the product were similar to those of Example 2, four isomers being formed from each of the olefins present in the feedstock.

Example 3B illustrates the use of another catalyst (Amberlyst XE-372) in the equipment of Example 3A and in conjunction with virgin (fresh) $C_{13}/C_{14}$ α-olefin as feedstock.

Amberlyst XE-372 is an aromatic, ring-chlorinated version of Amberlyst 15. It differs from the latter mainly in the fact that it has greater thermal stability; accordingly, the experiments with this resin were carried out at reactor temperatures of 140°–145° C. The system described above was operated for a total of 34 days (8-hour days) with the XE-372 resin. The breakdown of the 34 days of operation was as follows: initial cycle-17 days; 1st regeneration cycle-12 days; 2nd regeneration cycle-5 days. The total productivity for the 34 days of operation was 111.56 pounds of acetates per pound of catalyst. The actual weight of product made was 14.73 pounds from 87.7 pounds of feed. Structurally, the product was similar to that of Examples 2 and 3A, except for a somewhat higher content of the 2-isomers species relative to the other isomers.

Comparative Example 3C illustrates the attempted use of another resin (Amberlyst XE-365) as catalyst for the acid-olefin reaction. Amberlyst XE-365 is similar to Amberlyst 15 in chemical composition, but differs physically from both the former resin and the XE-372 resin in being less highly cross-linked, having less surface area, and having a lower free pore volume. The parameters, as promulgated by Rohm & Haas, are as follows:

| Resin | Internal Surface Area, m²/gm | Porosity (Pore Volume), % | Cross-link Density, % |
|---|---|---|---|
| Amberlyst 15 | 55 | 36 | 18–21 |
| XE-372 | 50 | 30–35 | 18–21 |
| XE-365 | 25 | 12 | 10–12 |

Operation of the reactor system of Examples 3A,B on fresh (virgin) $C_{13}/C_{14}$ α-olefin feedstock using XE-365 catalyst provided conversions of only 5–7% at temperatures as high as 150° C. and residence times as high as 30–35 minutes. Subjecting this resin to a typical regeneration procedure failed to improve the results. Clearly, XE-365 is not an acceptable catalyst for the acetic acid/detergent range olefin reaction and its lack of activity vis-a-vis Amberlyst 15 and XE-372 must derive from differences in physical rather than chemical characteristics. Without intending to be bound to any particular theory, it is believed that the smaller pore size of the XE-365 precludes diffusion of the relatively large olefin molecules into the resin matrix, so that the resin really does not behave as a macroreticular substance. In any case, this example demonstrates that not all macroreticular strong acid resins are useful as catalysts with these particular reactants in this step of the instant process.

EXAMPLE 4

This example provides further illustration of the preparation of secondary tridecyl and secondary tetradecyl alcohol acetates (mixed isomers) by the reaction of a 2:1 molar mixture of acetic acid and $C_{13}/C_{14}$ α-olefins in a fixed bed reactor using Amberlyst XE-372 as catalyst. At various times during the experiments, the feedstock was virgin α-olefin, recovered olefin, or a mixture of 2 parts recovered olefin and 1 part virgin olefin. In this example, however, the reactor used was a jacketed, 1"×12" type 316L stainless steel pipe packed with a 6" layer (35 grams) of Amberlyst 372 resin contained between two layers of glass beads (located at inlet and outlet of reactor) and supported on/restrained by fine mesh stainless steel screens. In place of the heated molecular sieve-containing feedstock "cleanup" column described in Example 2 there was used a similar heated (70°–80° C.) column packed with Amberlyst 15 resin. This column operated as a "pre-reactor," the function of which was to remove tramp metal ions, particularly iron, from the feedstock. The Amberlyst 15 resin in the pre-reactor is thus being utilized as an ion-exchange resin. This step is very desirable in order to maximize catalyst life in the main reactor. Reactor temperature was controlled by circulating a heat-exchange fluid of desired temperature through the jacket portion of the reactor. An alternate or supplemental reactor similar in design and temperature control mode to the first, but containing Amberlyst 15 resin rather than XE-372, was located in the process train between the "cleanup" column and the primary reactor. Flows through this alternate reactor could, if desired, be isolated from the primary reactor so that one reactor could be operated while the other was being regenerated. In the experiments of this example, the process stream flowed through this secondary reactor, but no reaction occurred at this point because the temperature was maintained below 100° C. Samples taken from the base of the secondary reactor during operation confirmed the fact that substantially all reaction was taking place in the primary reactor.

The above-described system was operated for a total of 63 days, of which the first 31 represented the initial cycle of catalyst usage, the next 21 the first regeneration cycle of catalyst usage, and the last 11 the second regeneration cycle of usage. During the initial cycle test, the operation was carried out on an around-the-clock basis (24 hours/day), except for one major planned shutdown (holiday/vacation period) and several minor unplanned shutdowns caused by power outages. During this initial cycle of resin usage, the feedstock was a 2:1 molar mixture of acetic acid and virgin (fresh) $C_{13}/C_{14}$ α-olefin. The reactor temperature ranged from 134°–140° C., the reactor pressure from 37–42 psig, and the reactor residence (contact) time from 20–31 minutes. For this initial cycle, productivity was 493.6 pounds of acetates/pound of resin with conversions (olefin basis) ranging from 15.4–31.9% of the theoretical. During the first regeneration cycle of resin usage, the feedstock was virgin α-olefin for days 1–8, a 2:1 w/w mixture of recovered:-virgin olefins for days 9–12, virgin olefin for days 13–15, 2:1 w/w recovered:virgin mixture for days 16–19, and virgin α-olefin for days 20–21. Over the course of this cycle of resin usage, reactor temperature ranged from 135°–142° C., reactor pressure from 40–43 psig, and residence time from 21–29 minutes. Operation during this cycle was on a 24 hours/day, 5 days/week basis. For this cycle of resin usage, productivity was 247.8 pounds acetates/pound resin, raising the cumulative productivity for the resin charge to 741.3 pounds/pound. Conversions (olefin basis) during the first regeneration cycle ranged from 12.3–36.6% of the theoretical. During the second regeneration cycle of resin usage, the feedstock used was virgin α-olefin for days 1-2, recovered olefin for days 3-6, and 2:1 recovered: virgin mixture for days 7-11. Reactor temperature during this cycle ranged from 135°-142° C., reactor pressure from 40-50 psig, and residence time from 19-25 minutes. Operation during this cycle was once again on a basis of 24 hours/day, 5 days/week. In this cycle of resin usage, productivity was 100.1 pounds acetates/pound resin with conversions (olefin basis) ranging from 14.8-34.7% of the theoretical. Cumulative productivity of the resin charge after three cycles of resin usage was 841.4 pounds/pound.

EXAMPLE 5

This example illustrates the basic concept of coproducing detergent range ($C_{13}/C_{14}$ in this case) 2° alcohols and butyl acetate via single pass, continuous transesterification (reactive distillation) of the precursor 2° alcohol acetates with n-butyl alcohol. The reactive distillation was carried out at atmospheric pressure in a 60-tray glass Oldershaw column (volumn of column approximately 55 ml.) mounted above a 300 ml. glass kettle which served as the "reboiler." A pre-heated mixture of refined $C_{13}/C_{14}$ 2° alcohol acetates (approx. 46/54 w/w %), made as described in the preceding examples, and tetraisopropyl titanate catalyst (Tyzor®TPT) was pump-fed into the top section of this column while excess n-butyl alcohol was simultaneously pump-fed through a vaporizing preheater into the bottom section of the column. The overhead material (distillate) from the column (a mixture of n-butanol and n-butyl acetate) was removed continuously on a "total make" basis, i.e., no reflux was carried on the column. A relatively constant volume (approx. 100 ml.) of liquid was maintained in the reboiler by continuous removal, from the base of the still, of a crude product stream at a rate such that a volume/time increment balance was maintained between the reactants fed to the column and the products removed therefrom. The crude product stream from the base of the still was collected in a chilled receiver in order to "quench" the reaction for analytical purposes. At selected time intervals the overhead and still bottom "makes" were collected, weighed and analyzed for composition by gas chromatography using a 40' Apiezon L (20%) on Chromasorb Q 60/80 chromatographic column. Prior to their analysis, the still bottoms stream samples were treated with water (approx. 1 g./10 g. of sample) to hydrolyze the catalyst residues to $TiO_2$ and to liberate the product 2° alcohols present as exchanged catalyst complex. The hydrolyzed samples were then centrifuged and the clear supernatant liquid layer was used for the GC analysis.

Operation of the above-described reactive distillation system is summarized in Table III; for comparative purposes, the results obtained from one experiment using a shorter distillation column (40 trays versus 60 trays) of otherwise identical design are included in the tabulated data. The data from this example demonstrate that the concept of continuous transesterification to coproduce detergent range 2° alcohols and low molecular weight esters is viable, but that conversion of the 2° alcohol acetates is incomplete even with a 60 tray column under conditions of simple single-pass operation. The best conversion achieved in this Example was 93 mol %; this conversion was attained under conditions wherein a larger excess of butanol reactant and a longer residence time in the column were used. This observation suggested the need for certain changes in both design and operation of the continuous still. Example 6, following, illustrates the attainment of significantly higher conversion levels through the use of higher butanol:fatty alcohol acetate ratios in conjunction with a pre-reaction step wherein the 2° alcohol acetate/catalyst feed mixture to the column in Example 5 was replaced by a partially reacted feed mixture.

TABLE III
CONTINUOUS TRANSESTERIFICATION OF REFINED $C_{13}/C_{14}$ 2° ALCOHOL ACETATES SIMPLE SINGLE PASS (W/O PREREACTION)

| | | | | | |
|---|---|---|---|---|---|
| Mol Ratio, BuOH:Ester | 3.51 | 3.53 | 3.41 | 3.07 | 4.52 |
| Catalyst[b]-TYZOR ® | TPT | TPT | TPT | TPT | TPT |
| Catalyst Conc. | | | | | |
| Wt. % in feed | 3.38 | 3.38 | 3.38 | 3.85 | 3.85 |
| Moles/Liter | 0.051 | 0.051 | 0.0515 | 0.062 | 0.051 |
| Feed Rates, cc/hr | | | | | |
| BuOH | 153.3 | 150 | 144 | 133.3 | 136.7 |
| Ester | 153.3 | 150 | 148 | 153.3 | 106.7 |
| Overall | 306.6 | 300 | 292 | 286.6 | 243.4 |
| Column Parameters: | | | | | |
| No. of Trays | 40 | 60 | 60 | 60 | 60 |
| Residence Time, mins. | 6.85 | 11.0 | 11.3 | 11.5 | 13.5 |
| Temperature Profile | | | | | |
| Reboiler | 225 | 225 | 202 | 203 | 197 |
| BuOH Feed | 152 | 152 | 152 | 152 | 149 |
| Ester/Catalyst Feed | 158 | 158 | 153 | 152 | 141 |
| Vapor (Overhead Make) | 117 | 117 | 117 | 117 | 117 |
| Bottom Tray | 148 | 148 | 145 | 133 | 133 |
| Tray No. 30 | 122 | — | — | — | — |
| Material Balance, % | 97.1 | 99.4 | 100.8 | 100.2 | 99.5 |
| Length of Run, hrs. | 1.5 | 1.0 | 1.25 | 1.5 | 1.5 |
| Product Stream, Wts., g. | | | | | |
| Overhead Make | 207.3 | 139.3 | 170.4 | 179.7 | 158.5 |
| Reboiler Effluent | 163.6 | 108.5 | 135.3 | 179.0 | 142.5 |
| Product Stream Compositions, Wt. % | | | | | |
| Overhead | | | | | |
| BuOH | 64.1 | 62.2 | 61.4 | 57.8 | 66.8 |
| BuAc[b] | 35.9 | 37.8 | 38.6 | 42.2 | 33.2 |
| Reboiler Effluent | | | | | |
| BuOH | 1.2 | 1.4 | 2.85 | 5.3 | 15.1 |
| BuAc | 0.71 | 0.55 | 0.90 | 1.6 | 2.2 |
| Fatty Alcohol | 80.8 | 84.85 | 87.55 | 80.1 | 75.0 |
| Fatty Acetate | 17.3 | 13.2 | 8.7 | 13.0 | 6.85 |
| Acetate Conv., Mol % | 84.8 | 87.0 | 92.3 | 88.0 | 92.9 |

[a]TPT = Tetraisopropyl Titanate
[b]Includes the small quantity of isopropyl acetate derived from catalyst exchange.

EXAMPLE 6

This example illustrates the coproduction of detergent range 2° alcohols and butyl acetate by continuous transesterification of the precursor 2° alcohol acetates with butanol in the presence of tetrabutyl titanate (Tyzor®TBT) catalyst under conditions wherein very high conversions are attained. The principal factor responsible for the higher conversions attained in this example vis-a-vis that of Example 5 is the use of a pre-reaction step wherein a minor portion of the overall butanol reactant charge is mixed with the fatty alcohol ester and catalyst and allowed to undergo partial reaction prior to entering the top of the still column as the column feed. In the experiments of this example, the pre-reaction step was conducted right in the feed line between the pump and the top of the still column. This was accomplished by using a jacketed feed line with a hot heat-exchange fluid circulating through the jacket.

The pertinent data of Example 6 are summarized in Tables IVA and IVB; the major difference in the two experiments was that the IVB runs were conducted at somewhat higher butanol: fatty ester mol ratios, both in the pre-reaction step and overall. The beneficial changes made in moving from the simple single-pass operations of Example 5 to the pre-reaction step, single-pass operation of Example 6 are apparent in a comparison of the conversions attained in the two examples. With the pre-reaction step, conversions were in the 93 mol % obtained from the simple single-pass operation. The results presented in Tables IVA and IVB demonstrate the viability of the concept of continuous transesterification as a route to detergent range 2° alcohols and low molecular weight esters.

TABLE IV A
CONTINUOUS TRANSESTERIFICATION OF REFINED $C_{13}/C_{14}$ 2° ALCOHOL ACETATES SINGLE PASS WITH PRE-REACTION STEP

| Mol Ratio, BuOH/Ester | | | | | |
|---|---|---|---|---|---|
| In Mixed Feed | 0.65 | 0.65 | 0.67 | 0.67 | 0.67 |
| Overall | 4.29 | 4.37 | 4.61 | 4.21 | 4.38 |
| Mixed Feed Composition, Wt. %[a] | | | | | |
| BuOH | 14.85 | 14.85 | 14.95 | 14.95 | 14.95 |
| Fatty Ester | 81.6 | 81.6 | 81.0 | 81.0 | 81.0 |
| Catalyst | 3.55 | 3.55 | 4.05 | 4.05 | 4.05 |
| Catalyst - TYZOR ® | TBT | TBT | TBT | TBT | TBT |
| Catalyst Conc. | | | | | |
| Wt. % on Ester | 4.4 | 4.4 | 5.0 | 5.0 | 5.0 |
| Mols/Liter | 0.047 | 0.047 | 0.052 | 0.055 | 0.054 |
| Feed Rates, cc/hr | | | | | |
| BuOH | 130 | 135 | 140 | 130 | 139.4 |
| BuOH/Ester/Catalyst | 150 | 152.5 | 150 | 155 | 158.6 |
| Residence Times, mins | | | | | |
| Pre-Reactor (Transfer Lines) | 19.0 | 18.5 | 18.3 | 18.7 | 17.8 |
| Continuous Still (60 Trays) | 11.6 | 11.3 | 11.2 | 11.4 | 10.9 |
| Still Temperature Profile, °C. | | | | | |
| Reboiler | 212 | 220 | 207 | 223 | 222 |
| BuOH Feed | 143 | 127 | 135 | 138 | 137 |
| Mixed Feed | 119 | 119 | 137 | 130 | 129 |
| Vapor (Overhead) | 117 | 117 | 117 | 117 | 117 |
| Bottom Tray | 146 | 146 | 146 | 139 | 147 |
| Material Balance, % | 101.3 | 99.7 | 101.2 | 99.9 | 97.7 |
| Length of Run, Hours | 1.0 | 2.0 | 1.0 | 2.0 | 2.08 |
| Product Stream weights, g | | | | | |
| Overhead | 140.6 | 285.9 | 148.1 | 283.1 | 305 |
| Still Bottoms | 94.4 | 189.1 | 94.7 | 188.8 | 196.7 |
| Product Stream Compositions, % | | | | | |
| Overhead | | | | | |
| BuOH | 68.2 | 68.0 | 67.9 | 67.9 | 68.1 |
| BuAc | 31.8 | 32.0 | 32.1 | 32.1 | 31.9 |
| Still Bottoms | | | | | |
| BuOH | 3.9 | 4.0 | 2.7 | 2.8 | 2.9 |
| BuAc | 0.72 | 0.72 | 0.51 | 0.52 | 0.52 |
| Fatty Alcohol | 92.3 | 92.2 | 93.8 | 93.7 | 93.6 |
| Fatty Ester | 3.1 | 3.1 | 3.0 | 3.0 | 3.0 |
| Acetate Conv., Mol % | 97.3 | 97.3 | 97.4 | 97.4 | 97.4 |

[a]Specific gravity on mixed feed = 0.855

TABLE IV B
CONTINUOUS TRANSESTERIFICATION OF REFINED $C_{13}/C_{14}$ 2°ALCOHOL ACETATES SINGLE PASS WITH PRE-REACTION STEP

| Mol Ratio, BuOH/Ester | | | | | |
|---|---|---|---|---|---|
| In Mixed Feed | 0.94 | 0.94 | 0.94 | 0.94 | 0.94 |
| Overall | 4.86 | 5.0 | 4.86 | 4.86 | 4.88 |
| Mixed Feed Composition, Wt. %[a] | | | | | |
| BuOH | 20.0 | 20.0 | 20.0 | 20.0 | 20.0 |
| Fatty Ester | 76.19 | 76.19 | 76.19 | 76.19 | 76.19 |
| Catalyst | 3.81 | 3.81 | 3.81 | 3.81 | 3.81 |
| Catalyst - TYZOR ® | TBT | TBT | TBT | TBT | TBT |
| Catalyst Conc. | | | | | |
| Wt. % on Ester | 5.0 | 5.0 | 5.0 | 5.0 | 5.0 |
| Mols/Liter | 0.051 | 0.05 | 0.051 | 0.051 | 0.051 |
| Feed Rates, cc/hr | | | | | |
| BuOH | 135 | 140 | 135 | 135 | 140 |
| BuOH/Ester/Catalyst | 155 | 155 | 155 | 155 | 160 |
| Residence Times, mins. | | | | | |
| Pre-reactor (Transfer Lines) | 18.3 | 18.0 | 18.3 | 18.3 | 17.7 |
| Continuous Still (60-Trays) | 11.2 | 11.0 | 11.2 | 11.2 | 10.8 |
| Still Temperature Profile, °C. | | | | | |
| Reboiler | 221 | 224 | 223 | 223 | 223 |
| BuOH Feed | 135 | 145 | 140 | 143 | 139 |
| Mixed Feed | 134 | 131 | 134 | 130 | 133 |
| Vapor (Overhead) | 117 | 117 | 117 | 117 | 117 |
| Bottom Tray | 147 | 140 | 147 | 139 | 140 |
| Material Balance, % | 101.3 | 98.9 | 98.9 | 98.9 | 97.9 |
| Length of Run, hours | 2.0 | 2.0 | 2.0 | 2.0 | 1.5 |
| Product Stream Wts. g | | | | | |
| Overhead | 298 | 293.4 | 286.3 | 286.9 | 222.9 |
| Still Bottoms | 188.7 | 189.7 | 188.7 | 188.2 | 142.0 |
| Product Stream Compositions, % | | | | | |
| Overhead | | | | | |
| BuOH | 71.1 | 70.8 | 69.9 | 70.0 | 70.1 |
| BuAC | 28.9 | 29.2 | 30.1 | 30.0 | 29.9 |
| Still Bottoms | | | | | |
| BuOH | 4.5 | 4.4 | 4.2 | 4.1 | 4.8 |
| BuAC | 0.56 | 0.56 | 0.56 | 0.57 | 0.61 |
| Fatty Alcohol | 92.5 | 92.6 | 92.7 | 93.1 | 93.1 |
| Fatty Ester | 2.4 | 2.4 | 2.6 | 2.25 | 2.6 |
| Acetate Conv., Mol % | 97.9 | 97.9 | 97.7 | 98.0 | 97.7 |

[a]Specific gravity on mixed feed = 0.852

EXAMPLE 7

This example is similar to Example 6 except that the $C_{13}/C_{14}$ 2° alcohol acetate used as reactant was crude product in this instance, whereas it had been refined material in the prior example. The crude product used as feed in this example was obtained by continuous stripping in laboratory prototype equipment of the "make" stream from the acetic acid/olefin reaction described in Examples 1–4. The crude reaction product was first continuously stripped of acetic acid at atmospheric pressure using a 5-tray column and subsequently continuously stripped of unreacted olefins at 180 mm Hg pressure in a 35-tray vacuum still. Thus, the material used as feedstock for the continuous transesterification reaction of this example was entirely representative of that which would be expected from a fully integrated, continuous operation.

Table V summarizes results obtained from pre-reaction mode, continuous transesterification using crude 2° alcohol acetates as feedstocks. Conversions attained in these experiments ranged from 94.6–96.0 mol %. The fact that these conversions are slightly below those obtained in experiments with refined 2°alcohol acetate feedstock is probably due to the use of lower overall butanol:fatty ester mol ratios in this case rather than to any difference in feedstock quality. In fact, the generally excellent results obtained with the crude acetate feedstock attest to the "cleanness" of the overall process.

TABLE V

SECONDARY ALCOHOL HYDROPHOBES PRE-REACTION MODE CONTINUOUS TRANSESTERIFICATION OF CRUDE $C_{13}/C_{14}$ OLEFIN ACETATES

|  | 9 | 10 | 11 | 3 | 5 | 6 |
|---|---|---|---|---|---|---|
| Pre-Reaction Feedstock | | | | | | |
| Reference: | | 53-RJK-19-CK-1 | | | 53-RJK-7-CK-1 | |
| Specific Gravity | | 0.847 | | | 0.849 | |
| Composition, Wt. % | | | | | | |
| Butanol | | 20.0 | 20.0 | | | |
| $C_{13}/C_{14}$ Olefin Acetate | | 76.2 | 76.2 | | | |
| TYZOR ® TBT Catalyst | | 3.8 | 3.8 | | | |
| Mol Ratios, Butanol/Olefin Acetate | | | | | | |
| In Pre-reaction Feedstock | | 0.91 | | | 0.91 | |
| Overall | 4.02 | 4.07 | 4.07 | 4.64 | 4.14 | 4.12 |
| Catalyst Conc., Mole/liter | | 0.055 | | 0.051 | 0.054 | 0.055 |
| Feed Rates, cc/hour | | | | | | |
| Pre-Reaction Feedstock | 185.5 | 185 | 185 | 177 | 175.4 | 180 |
| Butanol to Still | 132.7 | 135 | 135 | 148 | 130.8 | 133.3 |
| Residence Time, Mins. | | | | | | |
| In Pre-Reaction Zone | 29.2 | 29.3 | 29.3 | 31.5 | 30.9 | 31.5 |
| In Still Column | 10.2 | 10.1 | 10.1 | 10.1 | 10.6 | 10.3 |
| Operating Temperatures | | | | | | |
| Pre-reaction Zone | 128 | 126 | 125 | 110 | 112 | 133 |
| Reboiler | 228 | 219 | 226 | 222 | 217 | 219 |
| Pre-Reaction Feedstock | 133 | 121 | 116 | 122 | 121 | 115 |
| Butanol Feed | 132 | 134 | 133 | 130 | 133 | 133 |
| Vapor (Overhead Make) | 117 | 117 | 117 | 117 | 117 | 116 |
| Bottom Column Tray | 155 | 145 | 137 | 149 | 152 | 142 |
| Butanol Preheater | 148 | 149 | 148 | 149 | 151 | 151 |
| Pre-Reaction Feedstock Preheater | 155 | 155 | 154 | 154 | 155 | 156 |
| Pump Settings | | | | | | |
| Reboiler | | 45 | | 50 | 40 | 40 |
| Butanol Feed | | 50 | | 40 | 40 | 40 |
| Pre-reaction Feedstock | | 60 | | 60 | 60 | 60 |
| Run Length, Hours | 5.5 | 2.0 | 4.0 | 2.5 | 6.2 | 1.5 |
| Material Balance, Out/In, % | 98.5 | 102.2 | 97.5 | 101.6 | 93.5 | 95.2 |
| Product Stream Weights, g | | | | | | |
| Overhead | 850.9 | 332.1 | 211.7 | 382.4 | 971.1 | 226.0 |
| Reboiler Effluent | 581.2 | 618.3 | 419.5 | 281.4 | 575.3 | 145.7 |
| Overhead Make Composition, Wt. % | | | | | | |
| Butanol | 65.2 | 67.6 | 63.5 | 67.8 | 68.0 | 67.1 |
| Butyl Acetate | 34.8 | 32.4 | 36.5 | 32.2 | 32.0 | 32.9 |
| Reboiler (Still Bottom) Make Composition, Wt. % | | | | | | |
| Butanol | 11.57 | 11.19 | 10.87 | | | |
| Butyl Acetate | 0.75 | 0.62 | 0.79 | 7.87 | 3.28 | 5.19 |
| $C_{13}/C_{14}$ Alcohol | 83.64 | 83.37 | 82.76 | 0.92 | 0.37 | 0.79 |
| $C_{13}/C_{14}$ Acetate | 4.05 | 4.82 | 5.58 | 86.81 | 91.38 | 88.37 |
|  | | | | 4.40 | 4.97 | 5.66 |
| Olefin Acetate Conversion, Mol % | 96.0 | 95.3 | 94.6 | 95.9 | 95.7 | 94.9 |

EXAMPLE 8

The preparation of non-ionic surfactants from the 2° alcohol hydrophobes produced by the process of this invention involves no novel technology and is not a part of the process claimed in this invention. For purposes solely of demonstrating that hydrophobes produced by the process of this invention can be readily converted to high performance surfactants, Tables VI and VII, respectively, show data comparing the physical properties and performance characteristics of the seven and nine mol ethylene oxide adducts of a $C_{13}/C_{14}$ hydrophobe made by the process of this invention with those of two commercially produced surfactants, Tergitol ® 15 5-7 and 15 5-9, derived from a $C_{12}-C_{15}$ 2° alcohol hydrophobe made by a paraffin oxidation process.

TABLE VI

COMPARATIVE PHYSICAL PROPERTIES OF SURFACTANTS

| Physical Property | $C_{13}C_{14}$ Seven Mol Ethoxylate | $C_{13}/C_{14}$ Nine Mol Ethoxylate | Tergitol ® 15 S-7[a] | Tergitol 15 S-9[a] |
|---|---|---|---|---|
| Molecular Weight, Hydrophobe | 212 | 211 | 200 | 200 |
| Molecular Weight, Ethoxylate | 549 | 598 | 508 | 596 |
| Mols EO/Mol Hydrophobe | 7.65 | 8.78 | 7.0 | 9.0 |
| Specific Gravity, g/cc, 24° C. | — | 0.990 | 0.994 | 1.006 |
| Viscosity, CKS, 25° C. | 52.9 | 56.1 | 67 | 78 |
| Color, Pt/Co | 80 | 60–65 | 35 | 35 |
| Pour Point, °F. | 26.5 | 40.5 | 45 (max) | 55 (max) |
| Cloud Point, °C. 1% Solution | 41.5 | 60.2 | 35–40 (spec. range) | 57.5–62.5 (spec. range) |

TABLE VI-continued
COMPARATIVE PHYSICAL PROPERTIES OF SURFACTANTS

| Physical Property | Product | | | |
|---|---|---|---|---|
| | $C_{13}C_{14}$ Seven Mol Ethoxylate | $C_{13}/C_{14}$ Nine Mol Ethoxylate | Tergitol ® 15 S-7[a] | Tergitol 15 S-9[a] |
| PH, 1% Solution | — | 6.5 | 6–8 (spec. range) | 6–8 (spec. range) |
| Unreacted 2° Alcohol Content, % | 0.24 | 1.67 | Not Reported | Not Reported |

[a]TERGITOL ® 15 S-7 and 15 S-9 are the seven and nine mol ethoxylates

TABLE VII
COMPARATIVE PERFORMANCE CHARACTERISTICS OF SURFACTANTS

| Property Tested | Product | | | |
|---|---|---|---|---|
| | $C_{13}/C_{14}$ Seven Mol Ethoxylate | $C_{13}/C_{14}$ Nine Mol Ethoxylate | TERGITOL ® 15 S-7 | TERGITOL ® 15[a] S-9 |
| Foaming, 50° C.[a] | | | | |
| Initial Height, mm | 39 | 150 | 66 | 164 |
| After 5 min., mm | 21 | 10 | 20 | 10 |
| Wetting Time, Sec. 25° C.[b] | | | | |
| .05% Solution | 18.0 | 9.2 | 17.9 | 19.8 |
| 0.1% Solution | 6.9 | 3.7 | 5.9 | 6.9 |
| 0.2% Solution | 2.5 | 2.2 | 2.0 | 3.0 |
| Conc., % For 20 second wetting | 0.04 | 0.022 | 0.046 | 0.048 |
| Scouring, 50° C.[c] | | | | |
| Average % Detergency | 21 | 19 | 19 | 20 |

[a]By Ross Miles Test, ASTM D-1173-53; 0.2% Conc. in distilled water.
[b]Draves Test, AATCC 17-1974; 6 gm Cotton Skeins with 3 gm Hook
[c]% Detergency = $R_l$-$R_s$/$R_c$-$R_s$ where $R_l$ = Laundered Reflectance, $R_s$ = Soiled Reflectance and $R_c$ = Clean Reflectance; Test Fabrics Soil Cloth Style 7406: 0 0.1% Surfactant

EXAMPLE 9

This example describes a fully integrated, continuous process of the invention.

A preheated mixture of appropriate detergent range olefin (e.g., a $C_{13}/C_{14}$ mixture) and acetic acid (molar ratio of acid:olefins=2:1) is pumped through a series of two packed bed reactors containing Amberlyst 15 resin. The first bed, a stream-cleaning bed, is heated to 60°–70° C.; the second bed, a reactor bed, is heated to 114°–118° C. at about 50 psig pressure. The residence time in the reactor bed is approximately 25 minutes. The effluent from the reactor is a homogeneous, amber-colored liquid containing about 30% acetic acid, 54% $C_{13}/C_{14}$ olefins, and 16% $C_{13}/C_{14}$ secondary alcohol acetates.

The effluent from the above reactor bed is pumped into the middle portion of 10-tray stripping still operated at vapor temperature of 117° C., a kettle temperature of 240°–250° C. and a reflux ratio of 1.5:1. Acetic acid is removed overhead continuously while a mixture of $C_{13}/C_{14}$ olefins and $C_{13}/C_{14}$ secondary alcohol acetates is continuously removed from the base of the still. This still bottoms stream is dark amber in color and contains <0.1% acetic acid. Its composition is approximately 64:36 $C_{13}/C_{14}$ olefins: $C_{13}/C_{14}$ secondary alcohol acetates. The overhead stream from the stripping still is recycled back to the acid/olefin reactor bed.

The stripping still bottoms stream is preheated to ~150° C. and then pumped to a 30-tray refining still, the feed entering the column at the tray 20 point 2/3 of the way up the column. This still is operated at a pressure of 180 mm., a reflux ratio of 4.5:2, a residence time of 6–8 minutes, and a reboiler (kettle) temperature of 240° C. A stream containing 97.5–100% $C_{13}/C_{14}$ olefins is continuously removed from the top of the still, while a stream containing 96.9–99.5% $C_{13}/C_{14}$ secondary alcohol acetates is continuously removed from the reboiler. The overhead stream, comprised of both terminal and internal $C_{13}/C_{14}$ olefins, is recycled back to the olefin/acetic acid packed bed reactor. The kettle stream, comprised of $C_{13}/C_{14}$ secondary alcohol acetates, is used as feedstock in the next step of the process.

The still bottom stream from the above separation step is mixed with sufficient n-butanol and tetrabutyl titanate to give a transesterification feedstock of composition of weight:76.2% $C_{13}/C_{14}$ secondary alcohol acetates, 20.0% n-butanol, and 3.8% tetrabutyl titanate. This mixture is prereacted in a heated line (115°–128° C.) for about 30 minutes before passing into the top section of a 60-tray transesterification column which is fed at the bottom with preheated, boiling n-butanol. The overall mol ratio of n-butanol; $C_{13}/C_{14}$ secondary alcohol acetates is about 4.1:1 and the overall catalyst concentration is about 0.05–0.06 mol/liter. The ester exchange reaction occurs as the prereacted $C_{13}/C_{14}$ secondary alcohol acetate drops down the column counter-current to the boiling n-butanol. The column is operated at a reboiler (kettle) temperature of 225° C. and a vapor temperature of 116°–117° C. Feed rates are such as to give a residence time in the column of ~10–12 minutes. The column is operated on a total overhead make basis; the overhead stream is a butanol/butyl acetate mixture of about 65:35 weight ratio. The make rate from the reboiler (kettle) is adjusted as necessary to maintain a reboiler temperature of 225° C. The make stream from the reboiler is a mixture of n-butanol, n-butyl acetate, $C_{13}/C_{14}$ secondary alcohols, and $C_{13}/C_{14}$ secondary alcohol acetates in the approximate weight percentages of 10–12, 0.5–1, 82–84, and 4–6, respectively. Also contained in the kettle make stream, but not detected analytically by the GC method used, is a non-volatile titanate catalyst residue.

The "light" species (n-butanol and n-butyl acetate) present in the transesterification still bottoms stream are removed from this stream in an atmospheric pressure continuous "flash" still similar in design and operation to that used for the acetic acid stripping described above. Alternatively, the still can be operated under vacuum, if so desired. The overhead make stream contains n-butanol and n-butyl acetate in a weight ratio approximately 10:1. This stream is combined with the overhead make from the continuous transesterification still for subsequent processing.

The still bottoms stream from the above "flash" stripping distillation has a composition of approximately 79-81% $C_{13}/C_{14}$ secondary alcohols, 6-8% secondary alcohol acetates, 11-13% non-volatiles (catalyst residues) and 0.5-3.5% olefins and other miscellaneous unidentified species, such as diols and diesters. This stream is fed into a demister-equipped "flash-pot" type evaporator operated at a kettle temperature of 180° C., a pressure of 15 mm Hg, and a vapor temperature of 160°-165° C. Operation under these conditions affords an overhead make (distillate): evaporator bottoms (residue) ratio of about 2.5:1. The distillate portion has a composition of approximately 90% $C_{13}/C_{14}$ secondary alcohols, 7-9% $C_{13}/C_{14}$ secondary alcohol acetates, and 1-3% of olefins, diols, diesters, etc., as unidentified materials. The color of the distillate fraction is 20-30 Pt/Co and its specific gravity is 0.82-0.83 gm/cc. This stream represents product of acceptable quality for further processing. The evaporator bottoms stream, having a viscosity of about 40-50 cks and a gravity of 0.86-0.87, contains about a 2:1 ratio of volatile:non-volatile species, as judged by behavior in a gas chromatograph.

The evaporator bottoms stream from the "flash-pot" evaporator is passed into a wiped-film type evaporator for further recovery of product. This evaporator is operated at a temperature of 160°-180° C. and a pressure of 2-5 mm Hg. Under these conditions >95% of the "volatiles" present in the feed to the unit is removed as distillate similar in composition to that from the "flash-pot" evaporator, but of somewhat higher color (60-70 Pt/Co). Accordingly, this overhead stream is fed back into the "flash-pot" evaporator for ultimate recovery as acceptable quality product. The residues (non-volatiles) stream from the wiped-film evaporator consists predominantly of organic titanates and high boiling by-products, such as diols, diesters, etc. The organic titanates in this stream are still active transesterification catalysts. Accordingly, this stream is recycled back to the transesterification column after removal of a suitable purge stream to prevent a continuing build-up of high-boiling by-products in the process train.

We claim:

1. A continuous process for co-producing secondary alcohols of long-chain olefins and lower carboxylic acid esters, comprising the steps of:
   (A) passing a mixture of a long-chain α-olefin, and optionally the internal olefin isomers thereof, together with a lower carboxylic acid through a reaction zone in the presence of an amount sufficient to catalyze the conversion of said olefins and carboxylic acids to secondary alcohol carboxylates of an acidic heterogeneous catalyst under conditions at which the corresponding oxylation reaction will occur, thereby producing mixtures of isomeric secondary alcohol carboxylates;
   (B) recovering the mixture of isomeric carboxylates produced in step (A);
   (C) mixing the recovered carboxylates with a lower aliphatic alcohol in a pre-reaction zone in the presence of an amount sufficient to catalyze the pre-reaction of said carboxylates and lower aliphatic alcohol to said secondary alcohols of long-chain olefins and lower carboxylic acid esters of an ester exchange catalyst under conditions at which pre-reaction will occur;
   (D) after the pre-reaction, passing the recovered carboxylates and a lower aliphatic alcohol, wherein the molar concentration of lower aliphatic alcohol is greater than the molar concentration of said carboxylates, through a reactive distillation still in the presence of an amount sufficient to catalyze the conversion of said carboxylates and lower aliphatic alcohol to said secondary alcohols of long-chain olefins and lower carboxylic acid esters of an ester exchange catalyst under conditions at which the ester exchange will occur, thereby producing, as co-products, secondary alcohols of said long-chain olefins and carboxylates of said lower aliphatic alcohols; and
   (E) removing said carboxylates overhead and said secondary alcohols in the tails.

2. A process of claim 1 wherein the acidic heterogeneous catalyst comprises a copolymeric, high fluorine content aliphatic sulfonic acid, or a macroreticular, cross-linked sulfonated styrene/divinyl benzene copolymer.

3. A process of claim 1 wherein the olefin is a linear, unsubstituted α-olefin of from 8 to 14 carbon atoms.

4. A process of claim 3 wherein the α-olefin is a mixture of linear, unsubstituted olefins of from 8 to 14 carbon atoms.

5. A process of claim 4 wherein the α-olefin is a mixture of linear, unsubstituted olefins of from 12 to 14 carbon atoms.

6. A process of claim 3 wherein the linear, unsubstituted olefin comprises an α-olefin of from 8 to 14 carbon atoms and internal olefin isomers thereof.

7. A process of claim 1 wherein the lower carboxylic acid is a linear or branched alkyl or alkenyl carboxylic acid of from 1 to 5 carbon atoms in the non-carboxylic moiety.

8. A process of claim 1 wherein the lower carboxylic acid is selected from the group consisting of acetic acid, cyanoacetic acid, the mono-, di-, and tri-chloroacetic acids, methoxyacetic acid, trifluoroacetic acid, 3-mercaptomethyl propionic acid, acrylic acid, methacrylic acid, 2-cyanoacrylic acid, 2-chloroacrylic acid, and β-acryloxypropionic acid.

9. A process of claim 1 wherein the lower aliphatic alcohol is a linear, branched, or cyclic, alcohol of 1 to 8 carbon atoms.

10. A process of claim 1 wherein the alcohol is selected from the group consisting of methanol, ethanol, n-propanol, isopropanol, n-butanol, isobutanol, allyl alcohol, 2-cyanoethanol, 2-chloroethanol, 2-ethoxyethanol, 3-chloropropanol, 2-fluoroethanol, methallyl alcohol, 2-butenol, and 2-ethylhexanol.

11. A process of claim 1 wherein the acidic heterogenous catalyst is (1) a copolymeric, high fluorine content aliphatic sulfonic acid, or (2) a macroreticular, cross-linked sulfonated styrene/divinyl benzene copolymer.

12. A process of claim 1 wherein the ester-exchange catalyst is a titanium alcoholate.

13. A continuous process for co-producing secondary alcohols of long-chain olefins and lower carboxylic acid esters, comprising the steps of:
   (A) passing a mixture of a long-chain α-olefin, and optionally the internal olefin isomers thereof, and a lower carboxylic acid through a reaction zone in the presence of an amount sufficient to catalyze the conversion of said olefins and carboxylic acids to secondary alcohol carboxylates of an acidic heterogeneous catalyst selected from the group consisting of copolymeric high fluorine content aliphatic sulfonic acids and macroreticular, cross-linked sulfonated styrene/divinyl benzene copolymers having a cross-link density of about 18 to 21% and a pore volume of from about 30 to 35% under conditions at which the corresponding oxylation reaction will occur, thereby producing mixtures of isomeric secondary alcohol carboxylates;

(B) recovering the mixture of isomeric carboxylates produced in step (A);

(C) mixing the recovered carboxylates with a lower aliphatic alcohol in a pre-reaction zone in the presence of an amount sufficient to catalyze the pre-reaction of said carboxylates and lower aliphatic alcohol to said secondary alcohols of long-chain olefins and lower carboxylic acid esters of an ester exchange catalyst under conditions at which pre-reaction will occur;

(D) after the pre-reaction, passing the recovered carboxylates and a lower aliphatic alcohol, wherein the molar concentration of lower aliphatic alcohol is greater than the molar concentration of said carboxylates, through a reactive distillation still in the presence of an amount sufficient to catalyze the conversion of said carboxylates and lower aliphatic alcohol to said secondary alcohols of long-chain olefins and lower carboxylic acid esters of an ester exchange catalyst under conditions at which the ester exchange will occur, thereby producing, as co-products, secondary alcohols of said long-chain olefins and carboxylates of said lower aliphatic alcohols; and (E) removing said carboxylates overhead and said secondary alcohols in the tails.

14. The process of claim 1 in which the molar concentration of lower aliphatic alcohol is increased in an amount sufficient to increase the secondary alcohol carboxylate conversion.

15. The process of claim 13 in which the molar concentration of lower aliphatic alcohol is increased in an amount sufficient to increase the secondary alcohol carboxylate conversion.

* * * * *